United States Patent [19]

Robinson

[11] Patent Number: 5,352,208
[45] Date of Patent: Oct. 4, 1994

[54] SAFE NON-REUSABLE HYPODERMIC SYRINGE

[76] Inventor: Wilbur D. Robinson, 4571 W. Lake Rd., Canandaigua, N.Y. 14424

[21] Appl. No.: 983,053

[22] Filed: Nov. 30, 1992

[51] Int. Cl.5 ............................................. A61M 5/32
[52] U.S. Cl. .................................. 604/198; 604/111
[58] Field of Search ............... 604/192, 110, 111, 197, 604/198, 263, 187, 218; 128/919

[56] References Cited

U.S. PATENT DOCUMENTS

| | | | |
|---|---|---|---|
| 4,373,526 | 2/1983 | Kling | 604/198 X |
| 4,631,057 | 12/1986 | Mitchell | 604/198 |
| 4,655,751 | 4/1987 | Harbaugh | 604/198 |
| 4,702,738 | 10/1987 | Spencer | 604/198 |
| 4,747,837 | 5/1988 | Hauck | 604/198 |
| 4,810,248 | 3/1989 | Masters et al. | 604/192 |
| 4,846,796 | 7/1989 | Carrell et al. | 604/110 |
| 4,908,023 | 9/1990 | Yuen | 604/118 |
| 4,921,486 | 12/1990 | DeChellis et al. | 604/110 |
| 4,931,048 | 10/1990 | Lopez | 604/110 |
| 4,947,863 | 2/1990 | Haber et al. | 128/764 |
| 4,957,490 | 8/1990 | Byrne et al. | 604/197 |
| 4,978,343 | 6/1990 | Dysarz et al. | 604/195 |
| 5,015,234 | 9/1991 | Jullien | 604/110 |
| 5,019,044 | 4/1991 | Tsao | 604/110 |
| 5,030,208 | 1/1991 | Novacek et al. | 604/195 |
| 5,053,018 | 10/1991 | Talonn et al. | 604/198 |
| 5,057,079 | 10/1991 | Tiemann et al. | 604/110 |
| 5,057,087 | 10/1991 | Harmon | 604/198 |
| 5,066,277 | 2/1991 | Carrell et al. | 604/110 |
| 5,120,309 | 7/1992 | Watts | 604/110 |
| 5,125,908 | 8/1992 | Cohen | 604/192 |
| 5,154,698 | 10/1992 | Compagnucci et al. | 604/110 |
| 5,197,953 | 3/1993 | Colonna | 604/110 |

FOREIGN PATENT DOCUMENTS

| | | | |
|---|---|---|---|
| 2650187 | 2/1991 | France | 604/110 |
| 2654629 | 5/1991 | France | 604/110 |

Primary Examiner—C. Fred Rosenbaum
Assistant Examiner—Chalin Smith

[57] ABSTRACT

A simple, reliable, low cost hypodermic syringe, comprised generally of a barrel (12) and plunger and including a slidable protective sleeve (32) yieldably retained in an initial retracted position, whereby the capped needle end of the syringe is exposed and a warning band (18) is obscured. The sleeve (32) is movable after removal of the cap, (30) which had also served as an assembly tool, to an extended latched position, thereby enshrouding the needle, (10) and exposing said warning band (18). The user can add retentive resistance further opposing premature extension of the sleeve (32). Once the syringe is used the cap (30) can be safely used again to further isolate the needle, (10) within a structurally stable, and permanently extended sleeve (32).

12 Claims, 4 Drawing Sheets

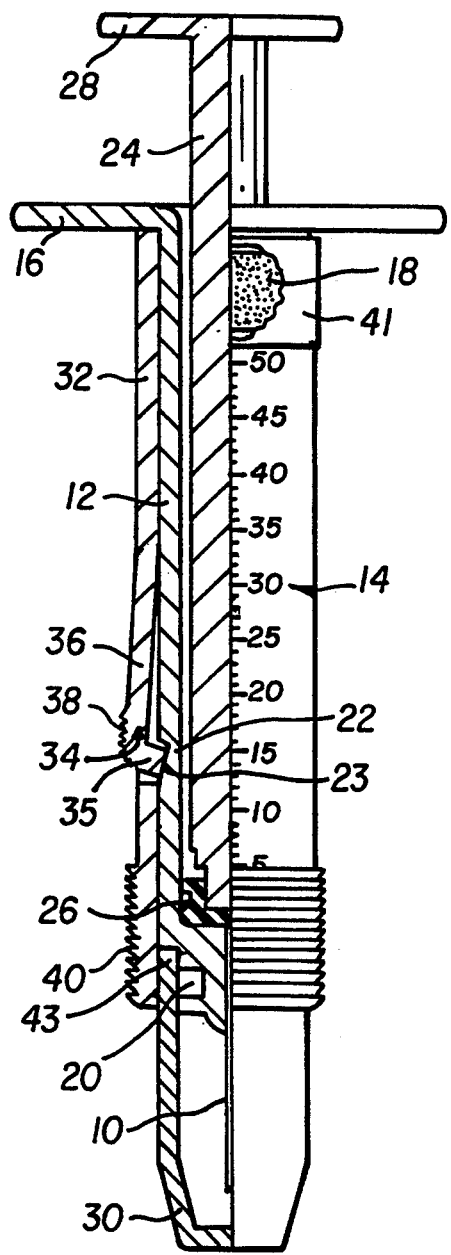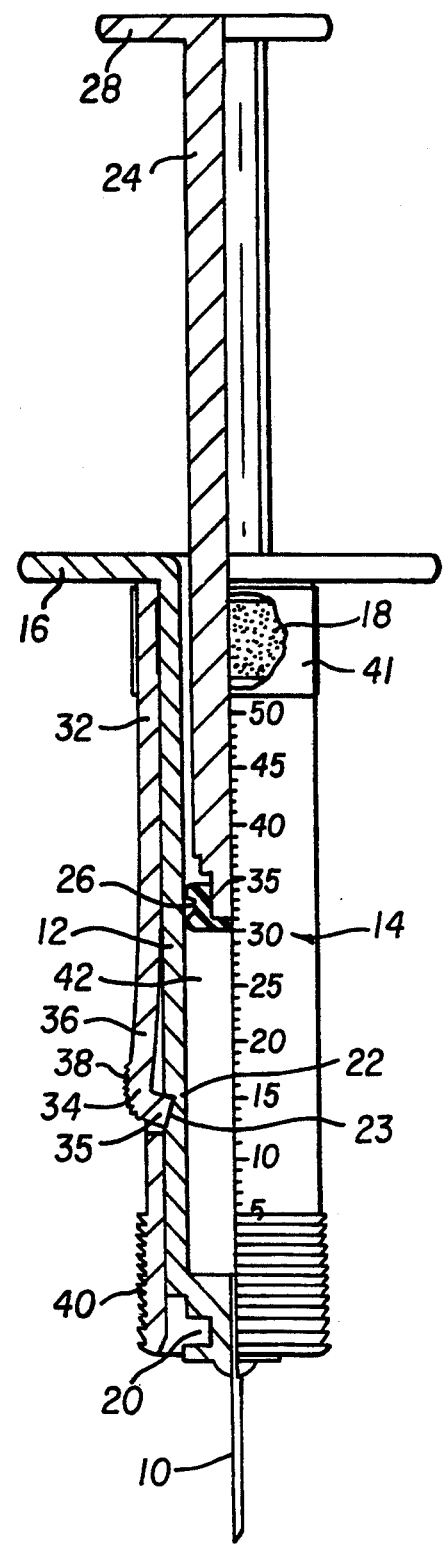
FIG. 5
FIG. 6

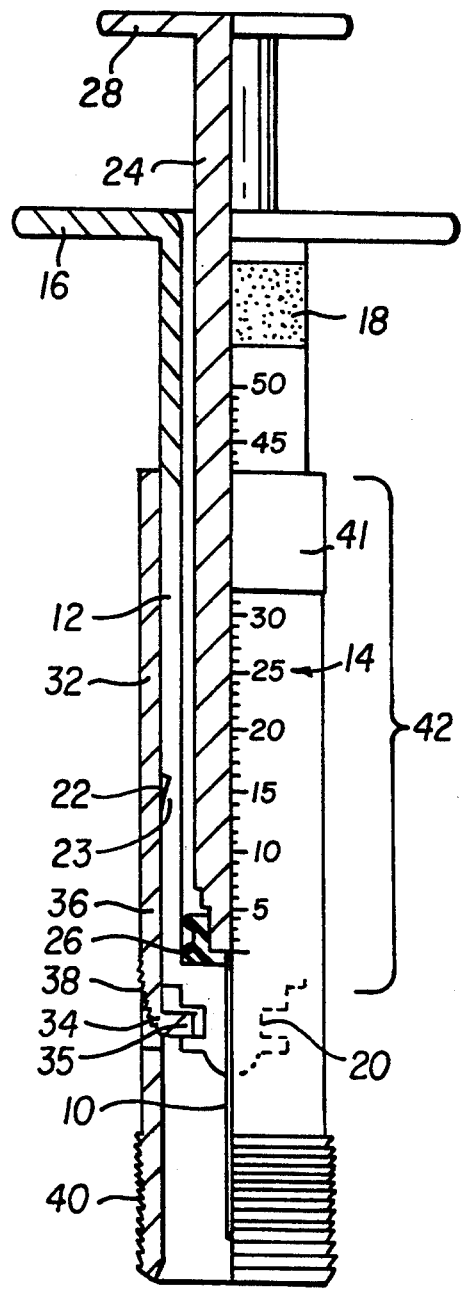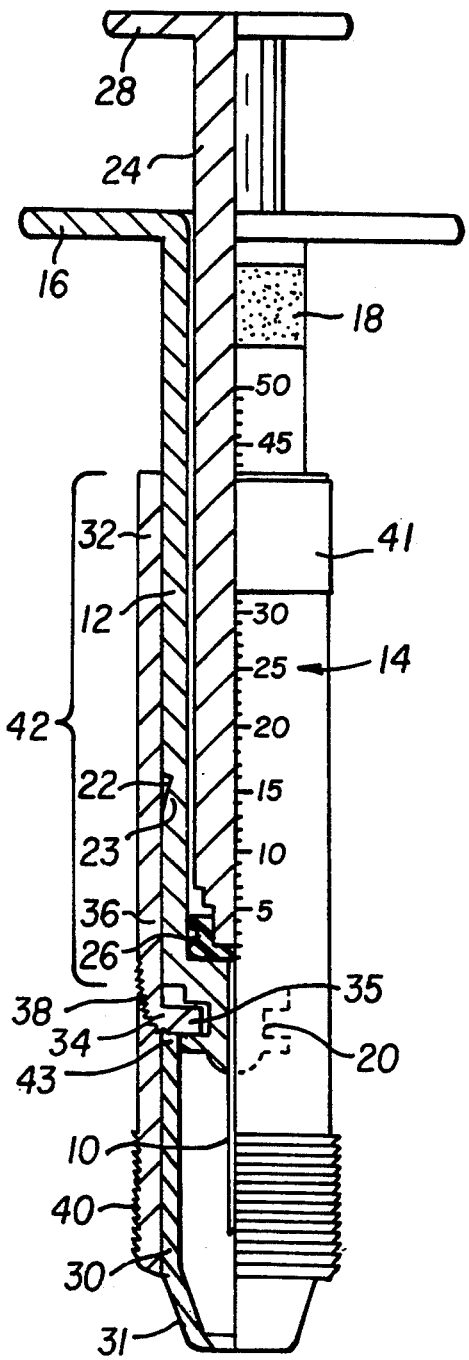
FIG. 7
FIG. 8

SAFE NON-REUSABLE HYPODERMIC SYRINGE

BACKGROUND OF THE INVENTION

1. Field of the Invention

The present invention relates to an improved hypodermic syringe and more particularly to a syringe with a means for insuring that the user or others will not accidentally be injured, thereby risking infection, once a needle has been used.

2. Description Relative to the Prior Art

In recent years, particularly since the onset of the AIDS epidemic and Hepatitis "B", many attempts have been made to provide hypodermic syringes with means for preventing accidental injury with a used needle, and for preventing a second use of a used needle. Various prior art references, for example U.S. Pat. Nos. 4,655,751, 5,197,953, 5,154,698, 5,057,079, 5,053,018, 4,810,248, 4,747,837, 4,702,738 and 4,631,057 show hypodermic syringes generally of the type having a slidable tubular sleeve that is in some cases initially retained in a retracted position by yieldable means, for example detent or latching. In the sleeve's retracted position the needle is exposed ready for use. After use, the sleeve is moved to an extended position in which it is latched, and in which the needle is surrounded by the sleeve to prevent accidental injury.

Whereas the primary objective of most of the prior art listed is common with the primary objective of the present invention, that is to protect patients and health care personnel against the potential mortal consequences of accidental skin puncture from a used hypodermic syringe, it is the present invention alone that in combination: First, recognizes a likelihood of an unwanted, premature extension of the protective sleeve during key procedural moments; secondly, provides structure by which a user may interact, by degree, to add to the restraint offered in opposition to a premature extension; thirdly, recognizes the importance of a simultaneous extension of the protective sleeve as the used needle is retracted from the patient; and lastly, provides structure to facilitate a smooth user release of the aforementioned restraint when, after an injection, it comes time to initiate a sleeve extension, simultaneous with needle withdrawal, without need for creating patient pain or discomfort, which might otherwise be the case, should any special user unlatching activity be required as pre-requisite to initiating the sleeve's extension. Primary examples of the referred to, key procedural moments, moments when a premature extension of the sleeve would be likely, are as follows: When removing and attaching needles; when withdrawing the plunger to entrap air; when inserting the needle tip into the medicine supply bottle; when withdrawing the plunger to load medicine into the syringe barrel; and when inserting the needle tip into a patient's body tissue.

U.S. Pat. No. 4,655,751, Harbaugh, appears indirectly to have recognized that there are key procedural times at which a premature extension would be likely, as Harbaugh has provided safeguards against such an extension. Harbaugh, provides ears on the sleeve which lock into pockets recessed into the syringe barrel and would prevent, by "locking", against an unwanted extension at the key procedural moments, as above outlined. In order to release the ears from the pockets at the appropriate time, to facilitate an intentional sleeve extension, the user flexes the somewhat resilient sleeve, distorting its generally cylindrical section into one or more oval in section. This unlatching activity is said to release the ears from the pockets.

The method of Harbaugh's release would seem improper, in terms of it being accomplished while the needle remained in patient tissue because: First there is the probability that a locking type mechanical release could malfunction, or hang up, thereby requiring a good deal of unlatching activity while the needle is deep in patient tissue, thus creating painful discomfort; and secondly because the very squeezing action required to release the ears from the pockets might also deform the resilient sleeve further than intended so that resistance would build at the interface between the sleeve and the barrel, in opposition to the very extension that is being attempted.

Harbaugh fails, as do the other prior art references, to: First, provide a structure which will allow a user interactive role in adding, by degree, to physical restrain in opposition to a premature extension of the protective sleeve; and secondly to develop the concept of a sleeve extension, simultaneous with a needle extraction from a patient, by providing structure which would provide a smooth release of the sleeve from its locked retracted position without special unlatching activity. The present invention alone provides these important features.

SUMMARY OF THE INVENTION

The present invention provides a simple, reliable, low cost device, comprised generally of a conventional syringe plus a slidable protective sleeve surrounding the syringe barrel. Said sleeve being, of one part, movable from an initial retracted position, from which a protective needle cap protrudes for removal before use, and a final extended position in which the sleeve surrounds the used needle in a manner to prevent injury. The sleeve can be yieldably held in its retracted position by a radially inward facing pawl (or pawls) member which is yieldably engaged with a detent groove circumscribing the syringe barrel. This pawl member is shaped so that a portion protrudes radially outward beyond the exterior surface of the sleeve when the sleeve is in it's retracted position, enabling the user to squeeze the pawl into a more positive engagement with the detent groove. This provides the user an absolute way to prevent accidental movement of the sleeve, away from its retracted position, during critical procedural moments.

In fact, due to the fact that the sleeve, as is later explained, is to be made of a springy resilient material with memory to return to its molded shape, any squeezing action, inadvertently applied anywhere upon the outer surface of the sleeve, and in particular in close proximity with the Pawl Grasping Surface 38, may very well deform the sleeve's generally resilient cylindrical section into a more oval shape, thereby increasing the frictional load between the sleeve 32, and the barrel 12 so as to increase the resistance which opposes the sleeves extension.

Furthermore, as the sleeve is extended, the invention also provides means whereby visible indicia is revealed warning of a used condition. The extension terminates as the sleeve locks into a position, protectively enshrouding the needle, leaving ample overlap with the barrel to assure a structurally stable relationship. With the sleeve in an extended position, the cap can be safely re-positioned over the needle, within the corresponding end of the extended sleeve, so as to isolate any possible needle borne contaminants without disengaging the sleeve's latched position.

Additionally, the design of the aforementioned needle cap enables its use not only as an initial shield, and as an after use needle isolation device, but also as a cost reducing assembly tool.

Various means for practicing the invention and other advantages and novel features thereof will be apparent from the following detailed description of illustrative preferred embodiments.

BRIEF DESCRIPTION OF THE DRAWINGS

Because the hypodermic syringe according to the present invention is generally symmetric about it's central axis, each figure is presented in a split drawing format; the right side of which is in side elevation, and the left side in section. FIGS. 1 through 8 illustrate various parts, and assemblies of parts, according to a preferred embodiment of the invention.

FIG. 1 shows the graduated syringe barrel and needle assembly; henceforth referred to as the barrel.

FIG. 2 shows a plunger and plunger seal integrated assembly.

FIG. 3 shows the configuration of the protective needle guard, or cap.

FIG. 4 shows the slidable protective sleeve.

FIG. 5 depicts the total assembly as it is configured for packaging, distribution, and use.

FIG. 6 depicts the syringe having been readied for injection.

FIG. 7 illustrates the syringe as it would appear immediately after the needle's withdrawal from body tissue, with the extended sleeve latched irreversibly to the barrel and protecting the needle.

FIG. 8 is the same as FIG. 7 except that the needle cap has been replaced in proximity of it's initial position.

DETAILED DESCRIPTION OF THE PREFERRED EMBODIMENTS

Figure 1:
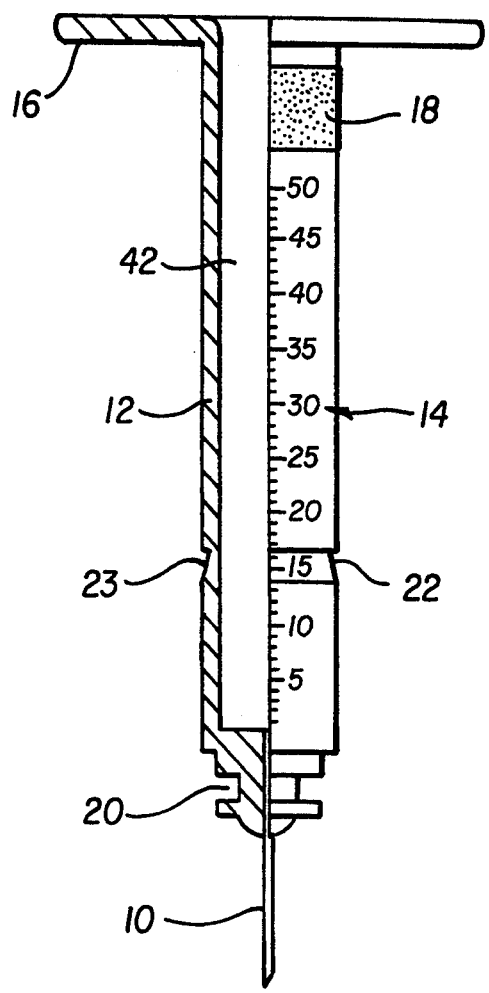

Referring first to FIG. 1, the illustrative preferred embodiment of the invention comprises a hollow fluid injection needle 10, injection molded into a generally transparent plastic syringe barrel 12, with graduated dosage indicia 14, and finger flanges 16, all of which are essentially the same as with today's state of the art products. In addition the barrel comprises: A used needle warning 18, which circumscribes barrel 12; annular tooth retaining groove 20 which circumscribes the needle end of barrel 12; and a annular detent groove 22 including a sloped surface 23 which circumscribes the barrel 12.

Figure 2:
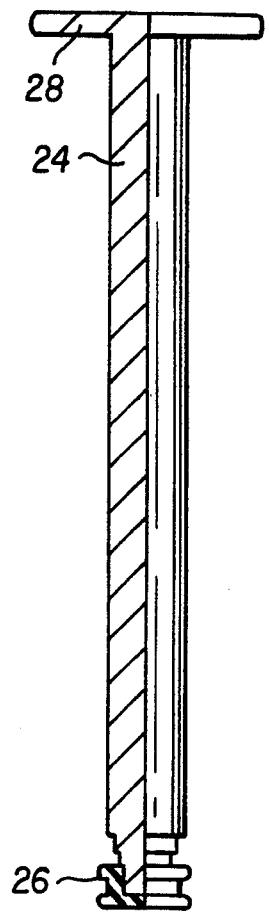

FIG. 2 shows a plunger assembly comprised of a plunger shaft 24, with a resilient plunger seal 26, and a thumb pad 28. It is identical to an assembly used in one of today's state of the art disposable syringes.

Figure 3:
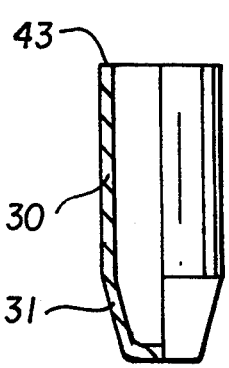

FIG. 3 shows a needle guard or cap 30. Unlike conventional caps, cap 30 includes a particular bullet like or tapered surface 31, a major advantage of which is explained later in connection with assembly procedures, in addition to an open entry end 43.

Figure 4:
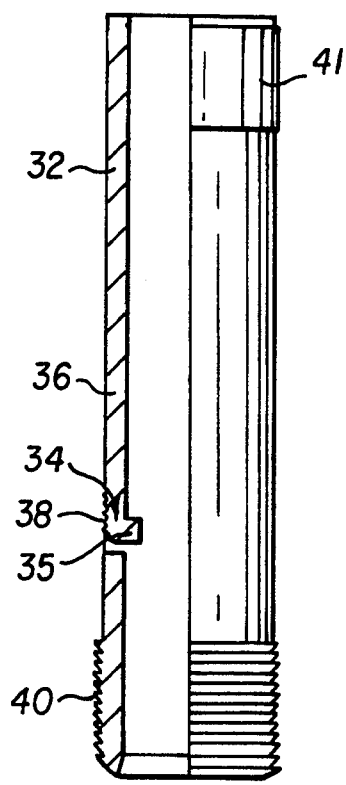

FIG. 4 shows a unitary sliding cylinder or sleeve 32, which is also a generally transparent plastic part, and which incorporates at least one radially inward facing latching pawl 34 bearing a resiliently supported pawl tooth 35, supported by a resilient pawl arm 36. An externally accessible roughened pawl grasping surface 38, is provided on the free end of the pawl arm 36 radially opposite the tooth 35. Additionally another, separate roughened sleeve grasping surface 40 circumscribes one end of the sleeve 32; and finally a opaque band 41 circumscribes the opposite end of the sleeve 32, as a means of obscuring from sight anything underlying it. The sleeve 32 can be injection molded from a thermoplastic material possessing qualities of transparency, hardness, sharp detail, and springiness, with memory to return to it's molded shape.

To initiate assembly of the foregoing four parts, the plunger assembly of FIG. 2 is first fully seated into the internal cavity 42 of the syringe barrel 12 of FIG. 1, thereby purging air from the internal cavity 42 of the barrel 12 out through the hollow needle 10. Then, in preparation for the assembly of the sleeve 32 onto barrel 12, the cap 30 is fitted onto the needle end of barrel 12, thereby sheathing the needle 10. Finally, the sleeve 32 is then slid past cap 30, which due to it's tapered surface 31, cams the radially inward facing pawl tooth 34 outward from the sleeve's central axis, allowing it to pass over the annular tooth retaining groove 20. Sleeve 32 is slid fully onto barrel 12, into a yieldable retracted position as shown in FIG. 5; thereby hiding the narrower warning band 18 beneath the wider opaque band 41, and seating a latching tooth 35 resiliently into the annular detent groove 22. The term yieldable means that sleeve 32 is held in the assembled, retracted position shown in FIG. 5, by means of detent and/or friction, but that it can later be slid relative to the syringe barrel 12 toward it's extended position as shown in FIG. 7 by user application of a relatively moderate axial force, without requiring special releasing or unlatching activity. This resistance to axial motion is sufficient to maintain the retracted position of sleeve 32 during routine handling of the syringe. Because all parts are generally cylindrical, and because grooves 20 and 22 circumscribe barrel 12, no rotational orientation is required between any of the parts at any time.

The procedure for use of the syringe, to inject medication into a patient as an example, is as follows: First, the sterile syringe is removed from it's protective wrapping, not shown. Then the needle cap 30 is removed from it's protective initial position and set aside for later use. Although this step exposes the user to possible injury by needle 10 for the first time, such an injury would pose no significant health threat as the needle 10 would not have yet been exposed to potential contamination.

Next, the user, grasps the syringe sleeve 32 between thumb and forefinger of one hand with either the thumb or the forefinger resting over the pawl grasping surface 38, and squeezes thereby seating tooth 35 firmly into the annular detent groove 22. This measure, which will henceforth be repeated each time the syringe is handled during a critical procedure, will provide the user with positive means for preventing premature extension of the sleeve 32 from it's retracted position. Inadvertent stray overlap of the thumb or forefinger from the pawl grasping surface to the sleeve surface will do not harm, as any distortion of the resilient nature of the sleeve material will merely serve to enhance the frictional resistance which occurs naturally between the sleeve and the barrel, thereby furthering the induced opposition to a premature extension of the sleeve. The user will next withdraw the plunger assembly with the free hand, by means of it's thumb pad 28, to a position corresponding to the volume of the intended dose of medicine. Calibrated dosage indicia 14, provided on the exterior wall of the syringe barrel, may be observed through the transparent portions of sleeve 32. The action thus described draws air into the internal cavity 42 of the barrel 12, equal in volume to the intended dosage. The syringe now appears as in FIG. 6.

Then, while still, or yet again, maintaining preventive measures opposing a premature extension of the sleeve 32, the user inserts the needle 10 into the medication bottle, not shown, and injects the entrapped air into the bottle by squeezing the thumb pad 28 toward the barrel's finger flanges 16 in the conventional way. Thus the amount of air, necessary to replace the intended withdrawal of medicine, has been placed in the bottle.

The user next loads the syringe with the prescribed dose of medicine as follows: With one hand the user prevents premature extension of the sleeve 32 as was explained above, and withdraws the plunger assembly of FIG. 2, the required distance out of the barrel's internal cavity 42 as seen in FIG. 6, by means of pulling on the thumb pad 28 with the thumb and forefinger of the free hand. Thus, with the syringe properly charged with the appropriate dose of medicine, the syringe is withdrawn from the bottle of medicine and with needle 10 pointed upward, any and all possible remaining air is purged from the syringe barrel 12 and/or the needle 10, in accord with conventional medical procedure.

With the syringe thus configured as in FIG. 6, ready for the injection of medicine into a patient, and with firm user interaction to prevent a premature extension of the sleeve 32, as discussed above, the needle 10 is inserted into the body tissue of the patient, the syringe normally aspirated, and the medicine is injected into the patient's body tissues, in the normal way, using the thumb, forefinger, and middle finger of either hand.

Following the injection, the user next holds the sleeve 32, without squeezing between the thumb and forefinger of the free hand, at any convenient location on sleeve 32 except coincident with the pawl grasping surface 38 thereby restraining the sleeve 32 against the patient's skin, not shown, and, by means of the finger flanges 16 already in appropriate contact with the pads of the index and middle fingers of the other hand, safely withdraws the needle 10 from the patient. Because sleeve 32 is held in it's position against the patient's skin while the remainder of the syringe is being retracted, the needle 10 becomes enshrouded within the protective confines of sleeve 32. The resiliently supported pawl tooth 35, having been cammed out of the releasable annular detent groove 22 due to the grooves sloped surface 23 and because the user has applied the appropriate axial forces, slides along the surface of the barrel 12, and snaps into a permanently locked engagement with the annular tooth retaining groove 20, thereby securing the needle 10 from all further potential for accidental contact. Should the user's grasp on the sleeve 32 slip inadvertently during the attempt to extend the sleeve 32, Sleeve Grasping Surface 40, is in place, and is of saw tooth shape so as to terminally oppose continued slippage of the user's grasp completely off of the end of the sleeve 32.

The needle 10 is thus safely enshrouded as per FIG. 7, within the extended sliding sleeve 32. Note that due to the full 360 degree circumferential nature of the latching arrangement, the latching engagement takes place regardless of the relative rotational orientation between the barrel 12, and the sliding sleeve 32. Equally important is the fact that after sleeve 32 and barrel 12 are latched together by means of resiliently supported pawl the seating of tooth 35 into annular tooth retaining groove 20, sufficient overlap 44 is provided between these two members to assure a structural integrity capable of withstanding considerable forces to which the syringe might be subjected before it's disposal.

Additionally, it should be noted that simultaneously with withdrawal of the needle 10 from the patient, and the simultaneous extension of sleeve 32 the warning 18 (red as an example), previously hidden by the wider circumferential obscurring opaque band 41 (yellow as an example), is exposed to view.

Finally, the needle cap 30 which had been set aside earlier, is retrieved by the user, and placed over the point of the needle 10, and within the extended protective sleeve 32, so as to remove all further threat of blood, body fluids, or tissues being accidently dispersed, (for example in the case where a needle should be accidentally dropped). This placement of the cap 30 to a position just short of it's initially assembled position, as best shown in FIG. 8, will now be possible to do with no danger of injury because the needle 10 has already been hidden from harms way within the protective sleeve 32. Further this placement of the cap 30 over the needle 10 cannot function to release resiliently supported pawl tooth 35 from it's latched relationship with the annular tooth retaining groove 20 because the cap's open entry end 43 squarely encounters the arresting face of the seated resiliently supported pawl tooth 35. The used syringe is now ready for appropriate disposal.

Figure 9:
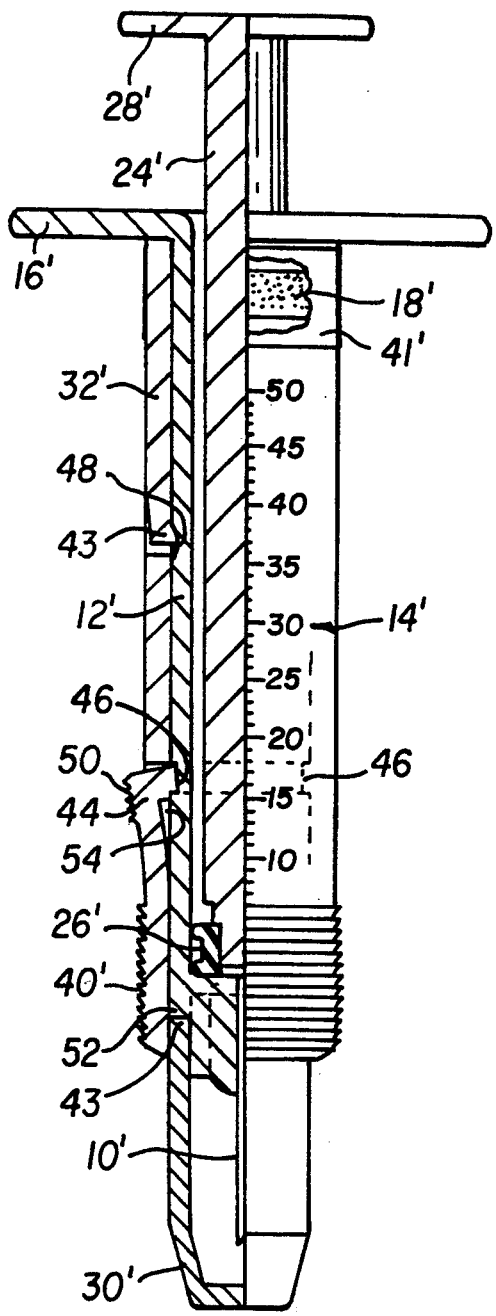
FIG. 9 depicts an alternate preferred embodiment of the invention, corresponding generally to FIG. 5, but showing a different arrangement for latching the sleeve in an extended position by use of at least two opposing pawls.

The alternate preferred embodiment of the present invention, shown in it's initial configuration in FIG. 9, is similar to the previously discussed preferred embodiment except that it uses at least two pawls rather than at least one; with extension arresting pawl 45 resisting extension of the sleeve 32' and with latching pawl 47 resisting the sleeve's motion onto the barrel 12'. This arrangement removes the need to provide the circumferential pawl retaining groove 20 of the preferred embodiment (shown in FIG. 1), but does require a annular extension arresting groove 46 to be molded into the surface of the syringe barrel 12' instead. This annular extension arresting groove 46 will receive extension arresting pawl 45 as shown in FIG. 10, so as to terminate the extension of sleeve 32' as the needle is withdrawn from the patient back into the protection of the extending sleeve 32' (Similarly as shown in FIG. 10 but without cap 30').

As can best be seen in FIG. 9, because of the location of the arresting groove 46 on barrel 12', it also serves as a means of detent for latching pawl 47, to yieldably resist premature extension of the sleeve 32', from the initially retracted or assembled position. Similarly the annular detent groove 48, surrounding barrel 12' will provide additional resistance when sleeve 32' is in it's retracted position, as a result of it's yieldable relationship with extension arresting pawl 45. The roughened pawl surface 50 and the shape of latching pawl 47 will protrude radially beyond the exterior cylindrical surface of the sleeve 32' when the sleeve 32' is in it's initially retracted position, so that the latching pawl 47 can be squeezed by the user, through use of the thumb and forefinger of one hand, in a manner similar to that explained at length for the previously discussed preferred embodiment, thereby providing the user with the same positive control to prevent premature extension of the sleeve 32'. Inadvertent stray overlap of the thumb or forefinger from the latching pawl 47, roughened pawl surface 50, to the surface of sleeve 32' will do no harm, as any resulting distortion of the resilient nature of the material of sleeve 32' will merely serve to enhance the frictional resistance which occurs naturally between the sleeve 32' and the barrel 12', thereby furthering the induced opposition to a premature extension of the sleeve 32'.

Figure 10:
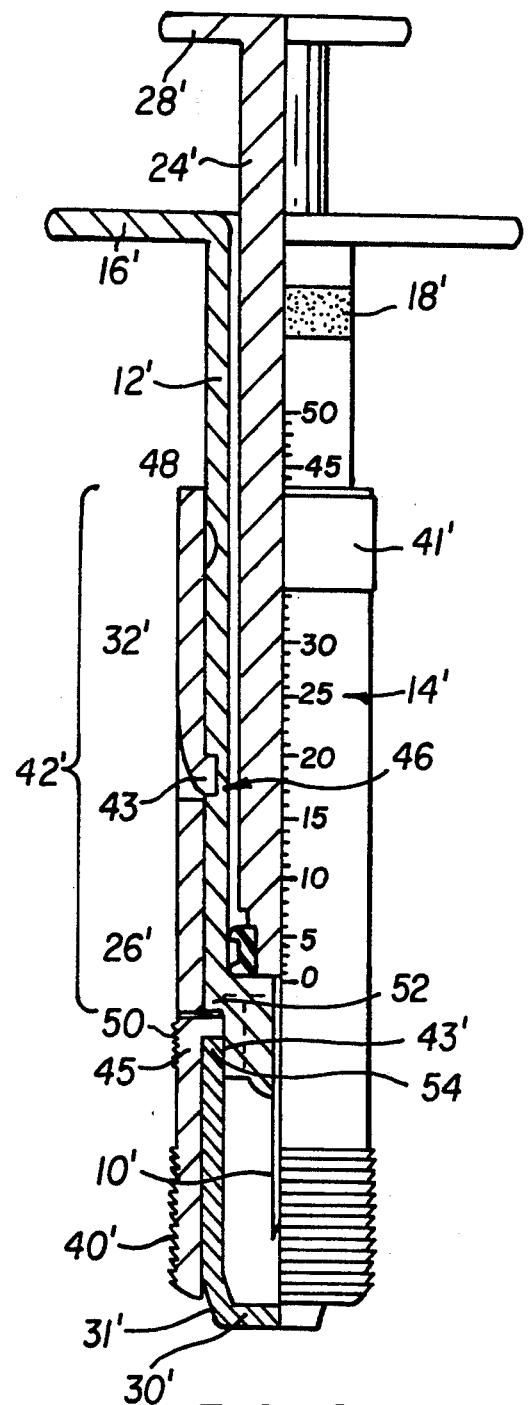
FIG. 10 shows the alternative preferred embodiment, as configured after use, and recapped.

As can best be seen in FIG. 10, upon full extension of the sleeve 32', as extension arresting 45 engages with annular extension arresting groove 46 and latching pawl 47 snaps radially inward off the needle barrel end corner 52 of the syringe barrel 12', preventing the return of the sleeve 32' onto the barrel 12'.

In examining the after use configuration, shown in FIG. 10, it becomes clear that the inner surface of the resilient arm that carries latching pawl 47 must have a step or notch 54, formed into it so that any effort to return the cap 30' to a position further isolating needle 10', can not undesirably cam the latching pawl 47 radially outward thereby enabling the sleeve 32' to be returned to it's initially retracted position so that the syringe could be used a second time.

The invention has been described in detail with particular reference to preferred embodiments thereof, but it will be understood that variations and modifications can be effected within the spirit and scope of the invention. For example, it should be understood that while the invention is described in terms of a hypodermic syringe being used to inject medication into body tissue, the invention also encompasses the use of the syringe for removing blood or other body fluids.

What is claimed is:

1. An improved hypodermic syringe of the type comprising:

a medication barrel, being generally conventional, rigid, and transparent, provided at one end with a needle and at its opposite open end with a pair of finger flanges, said barrel including graduated dosage indicia located on its exterior cylindrical surface; a plunger slidably received within said barrel; and a removable cap initially surrounding and protecting said needle;

a sleeve, being generally cylindrical, transparent, and made of a resilient plastic, slidably surrounding said barrel and movable between an initial retracted position, in which said needle and said cap project beyond the adjacent end of the retracted said sleeve, and a final extended position, said cap having been removed, in which the extended said sleeve protectively surrounds said needle;

a yieldable restraining means for yieldably restraining said sleeve in said initial retracted position; said yieldable restraining means comprising an annular detent groove provided with a sloped face, said annular detent groove being shaped essentially as a portion of a cone, machined, molded, or otherwise formed into, and surrounding said barrel, and a cooperative pawl arm, carried resiliently by said sleeve essentially in a location central to the length of said sleeve; said pawl arm being provided with a resiliently supported pawl tooth, resiliently and yieldably receivable in said annular detent groove; said yieldable restraining means also including a restraining frictional force which will occur naturally at an interface between the contacting surfaces of said sleeve and said barrel; all said yieldable restraining means providing but a light restraint in opposition to a user, intent on initiating an extension of said sleeve from said initial retracted position by application of opposing axial forces between said sleeve and said barrel, said light restraint capable of being easily and smoothly overridden by said user; said syringe being further characterized by;

an extension opposing means, externally accessible, whereby said user may manually grasp and squeeze said syringe so as to create additional restraint in opposition to the likelihood of a premature extension of said sleeve from said initial retracted position; said extension opposing means including external access to a pawl grasping surface located on the exterior surface of said pawl arm, manually graspable to enable said user to squeeze said resiliently supported pawl tooth into a more positive cooperative engagement with said annular detent groove; and said extension opposing means also including any resultant stray peripheral squeezing of the resilient cylindrical section of said sleeve, in proximity of said pawl arm, which may cause a flexing deformation of the generally thin resilient cylindrical section of said sleeve, into one more generally oval in section, thereby increasing said restraining frictional force which must occur naturally at said interface between the contacting surfaces of said sleeve and said barrel; and a latching means, responsive to axial movement of said sleeve to said final extended position, for permanently latching said sleeve, both terminally and irreversibly, in said final extended position; said latching means comprising an annular tooth retaining groove, machined, pressed, or molded into, and surrounding said barrel, adapted to permanently receive said resiliently supported pawl tooth, both terminally and irreversibly, when said sleeve reaches said final extended position.

2. The invention described by claim 1, in which generally transparent said barrel is provided with an alerting means supporting a system to forewarn of a used needle condition, said alerting means comprising a warning band, of warning color, superimposed upon or molded integrally into said barrel, and circumscribing said barrel in a strategic location cooperative with said sleeve whereby said warning band is obscured when said sleeve is in said retracted position, and exposed for visual observation whenever said sleeve is in said extended position.

3. The invention described by claim 1, in which generally transparent said sleeve is provided with an obscuring means supporting a system to forewarn of a used condition of said syringe, said obscuring means comprising an opaque band, superimposed upon or molded integrally into said sleeve, and circumscribing said sleeve in a strategic location cooperative with said barrel whereby said warning band is obscured by said opaque band whenever said sleeve is in said initial retracted position, and exposed for visual observation whenever said sleeve is in said final extended position.

4. The invention described by claim 1, in which the structure of said cap provides a camming means, said camming means comprised of a nose section, specifically shaped like a tapered cylinder, or a portion of a cone, whereby said nose section will serve to cam said resiliently supported pawl tooth, radially outward to enable it to carry past said annular tooth retaining groove, as said sleeve is initially slid onto said barrel from the needle end thereof, said camming means being provided as a measure to support low assembly costs.

5. The invention described by claim 1, in which said cap provides a safe recapping means; said safe recapping means comprised of a sufficiently long structure of said cap, whereby said user may safely recap said needle, being able to handle and fit said sufficiently long structure of said cap, protectively within the shielding envelope provided by said final extended position of said sleeve, while said cap remains unable to disengage said resiliently supported pawl tooth from said annular tooth retaining groove because the square face of said resiliently supported pawl tooth, seated into said annular tooth retaining groove, squarely abuts and confronts the squarely structured entry orifice of said cap, thereby limiting the onward movement of said cap, as said cap is received within said sleeve, said sleeve being in said final extended position; the purpose of said safe recapping means being to isolate possible needle-borne patient fluids.

6. The invention described by claim 1, in which the ability of said user to override said light restraint, in initiating an extension of said sleeve from its said initial retracted position, is facilitated by a slip reducing means, said slip reducing means comprising a sleeve grasping surface shaped in a saw tooth form so as to terminally oppose, slippage of a physical grasp of said user completely beyond the end of said sleeve located nearest said needle, during any said user attempt to extend said sleeve through the application of sleeve extending axial forces oppositely directed between said sleeve and said barrel.

7. An improved hypodermic syringe of the type comprising:

a medication barrel, being generally conventional, rigid, and transparent, provided at one end with a needle and at its opposite open end with a pair of finger flanges, said barrel including graduated dosage indicia located on its exterior cylindrical surface; a plunger slidably received within said barrel; and a removable cap initially surrounding and protecting said needle;

a sleeve, being generally cylindrical, transparent, and made of a resilient plastic, slidably surrounding said barrel and movable between an initial retracted position, in which said needle and said cap project beyond the adjacent end of the retracted said sleeve, and a final extended position, said cap having been removed, in which the extended said sleeve protectively surrounds said needle;

a yieldable restraining means for yieldably restraining said sleeve in said initial retracted position; said yieldable restraining means comprising; first, a cooperative association between an extension arresting pawl carried resiliently by said sleeve, and an annular restraining groove, machined, molded, or otherwise formed into, and circumscribing said barrel, and so formed to provide a camming like release of said extension arresting pawl, when said sleeve is extended forward out of said initial retracted position; secondly, a cooperative association between a latching pawl also resiliently carried by said sleeve, and an annular extension arresting grove, also machined, pressed, or molded into, and circumscribing said barrel, both said extension arresting pawl, and said latching pawl being located more or less in the central third section of said sleeve axially so as to be easily graspable; and lastly, said yieldable restraining means also including a restraining frictional force which will occur naturally at an interface between the contacting surfaces of said sleeve and said barrel; all said yieldable restraining means providing but a light restrain in opposition to a user, intent on initiating an extension of said sleeve from said initial retracted position by application of opposing axial forces between said sleeve and said barrel, said light restraint capable of being easily and smoothly overridden by said user; said syringe being further characterized by;

an extension opposing means, externally accessible, whereby said user may manually grasp and squeeze said syringe in a manner which will create a more positive restraint in opposition to the likelihood of a premature extension of said sleeve from said initial retracted position; said extension opposing means including external access to a latching pawl grasping surface located on the exterior surface of said latching pawl, manually graspable to enable said user to squeeze said latching pawl into a more positive engagement with said annular extension arresting groove; and said extension opposing means also including any resultant stray peripheral squeezing of the resilient cylindrical section of said sleeve, in proximity of said latching pawl grasping surface, which may cause a flexing deformation of the generally thin resilient cylindrical section of said sleeve, into one more generally oval in section, thereby increasing said restraining frictional force which must occur naturally at said interface between the contacting surfaces of said sleeve and said barrel; and a latching means, responsive to axial movement of said sleeve to said final extended position, for permanently latching said sleeve, terminally and irreversibly, into said final extended position; said latching means comprising first a cooperative association between said annular extension arresting groove and said extension arresting pawl, whereby said extension arresting pawl comes terminally at rest within said extension arresting groove, and secondly a cooperative association between a barrel end corner, and said latching pawl, whereby said latching pawl irreversibly drops off said barrel end corner, when said sleeve reaches said final extended position.

8. The invention described by claim 7, in which generally transparent said barrel is provided an alerting means in support of a system to forewarn of a used needle condition, said alerting means comprising a warning band, of warning color, superimposed upon or molded integrally into said barrel, and circumscribing said barrel in a strategic location cooperative with said sleeve whereby said warning band is obscured when said sleeve is in said initial retracted position, and exposed for visual observation whenever said sleeve is in said final extended position.

9. The invention described by claim 7, in which generally transparent said sleeve is provided an obscuring means in support of a system to forewarn of a used condition of said syringe, said obscuring means comprising an opaque band, superimposed upon or molded integrally into said sleeve, and circumscribing said sleeve in a strategic location cooperative with said barrel whereby said warning band is obscured by said opaque band whenever said sleeve is in said initial retracted position, and exposed for visual observation whenever said sleeve is in said final extended position.

10. The invention described by claim 7, in which the structure of said cap provides a camming means, said camming means comprised of a nose section, specifically shaped like a tapered cylinder, or a portion of a cone, whereby said nose section will serve to cam said latching pawl radially outward so as to enable said latching pawl to pass over said barrel end corner as said sleeve is initially slid onto said barrel from the needle end thereof, said camming means being provided as a measure to support low assembly costs.

11. The invention described by claim 7, in which said cap provides a safe recapping means; said safe recapping means comprised of a sufficiently long structure of said cap, whereby said user may safely recap said needle, being able to handle and fit said sufficiently long structure of said cap, protectively within the shielding envelope provided by said final extended position of said sleeve, while said cap remains unable to cam said latching pawl outward so as to enable it to clear said barrel end corner, because the square face of the oncoming opening to said cap abuts squarely into a notch, said notch having been made part of the shape of the radially inward facing surface of said latching pawl, as said cap is received within said sleeve, said sleeve being in said final extended position; the purpose of said safe recapping means being to isolate possible needle-borne patient fluids.

12. The invention described by claim 7, in which the ability of said user to override said light restraint, in initiating an extension of said sleeve from its said initial retracted position, is facilitated by a slip reducing means, said slip reducing means comprising a sleeve grasping surface shaped in a saw tooth form so as to terminally oppose, slippage of a physical grasp of said user completely beyond the end of said sleeve located nearest said needle, during any said user attempt to extend said sleeve through the application of sleeve extended axial forces, oppositely directed, between said sleeve and said barrel.

* * * * *